US00PP20670P3

(12) United States Plant Patent
Renault et al.

(10) Patent No.: US PP20,670 P3
(45) Date of Patent: Jan. 26, 2010

(54) ***HYDRANGEA* PLANT NAMED 'RENHY'**

(50) Latin Name: *Hydrangea paniculata*
Varietal Denomination: RENHY

(76) Inventors: Jean Renault, Le Brin D'Eau, 53120 Gorron (FR); Thierry Renault, Rue Ambroise Paré, 53120 Gorron (FR); Eric Renault, Le Petit Cour Janvier, Ambrières les Vallées (FR)

( * ) Notice: Subject to any disclaimer, the term of this patent is extended or adjusted under 35 U.S.C. 154(b) by 0 days.

(21) Appl. No.: 11/824,339

(22) Filed: Jun. 28, 2007

(65) Prior Publication Data

US 2009/0007306 P1 Jan. 1, 2009

(51) Int. Cl.
*A01H 5/00* (2006.01)

(52) U.S. Cl. ..... Plt./250

(58) Field of Classification Search ..... Plt./250
See application file for complete search history.

(56) References Cited

PUBLICATIONS

Upov Rom GTITM Computer Database, GTI Jouve Retrieval Software 2008/2 Citations for 'RENHY'.*

* cited by examiner

*Primary Examiner*—Wendy C. Haas

(57) ABSTRACT

A new cultivar of *Hydrangea, Hydrangea paniculata* 'RENHY', characterized by its large panicles of sterile flowers that emerge white and change to pink and finally to a red with maturity with the red coloration lasting about 3 to 4 weeks, its continuous flush of new flowering stems that give an overall multicolored effect in late summer to early fall, and its plant habit that changes from erect in early summer to cascading as the season progresses.

2 Drawing Sheets

Genus/species: *Hydrangea paniculata.*
Varietal denomination: 'RENHY'.

BACKGROUND OF THE INVENTION

The present invention relates to a new and distinct cultivar of *Hydrangea paniculata* and will be referred to hereafter by its cultivar name, 'RENHY'. 'RENHY' represents a new deciduous shrub grown for landscape use.

The new *Hydrangea* resulted from a controlled breeding program that commenced in 1987 in Gorron, France with the objective of obtaining a selection of *Hydrangea paniculata* that blooms early in the season with red, sterile flowers. The inventors started the breeding program by self-pollinating *Hydrangea paniculata* 'Unique' (not patented) and the parents of 'RENHY' were unnamed proprietary seedlings that arose after seven series of subsequent crosses. 'RENHY' was selected as a single unique plant amongst the progeny in Gorron, France in 2002.

Asexual reproduction of the new cultivar was first accomplished by softwood cuttings in May of 2003 by the inventors in Gorron, France. The characteristics of this cultivar have been determined to be stable and are reproduced true to type in successive generations.

SUMMARY OF THE INVENTION

The following traits have been repeatedly observed and represent the characteristics of the new cultivar as observed for 5 years in Gorron, France. These attributes in combination distinguish in 'RENHY' from other varieties of *Hydrangea* known to the inventor.

1. 'RENHY' blooms with large panicles of flowers that emerge white in mid summer, changing to pink after about 2 weeks and subsequently change to red or burgundy (depending on night temperature). The red coloration is retained for 3 to 4 weeks before turning brown.
2. 'RENHY' blooms on new growth and new inflorescences appear in late summer; the changing coloration at different stages of flower development provides for various color stages to exist simultaneously and imparts a multicolored effect in late summer.
3. The flowers of 'RENHY' have been observed to be sterile under the conditions tested.
4. The habit of 'RENHY' is erect early in the season and becomes supple and cascading later in the season under the weight of the mature flowers.
5. 'RENHY' blooms from mid July to mid October in France.
6. 'RENHY' is cold hardy to U.S.D.A. Zone 4 and blooms are frost tolerant.

Comparison to other *Hydrangea paniculata* cultivars: 'Unique', the parent of the parent plants of 'RENHY', is similar in having large white flowers, however the flowers turn light pink in late summer rather than red, some of the flowers are fertile, and the plant habit is very erect. 'RENHY' can also be compared to 'Grandiflora' (not patented) and 'Pinky Winky' (not patented). 'Grandiflora' also has large white flowers, however they are all fertile flowers and the flowers are pink for only a short period time. 'Pinky Winky' also has white flowers that are pink and red for only a short period of time and has a habit that is more erect than 'RENHY'.

BRIEF DESCRIPTION OF THE DRAWINGS

The drawings presented are digital photographs taken of plants 5 years in age in Gorron, France.

FIG. 2 is a side view of 'RENHY' and presents the color of the inflorescences in late summer while

Figure 1:
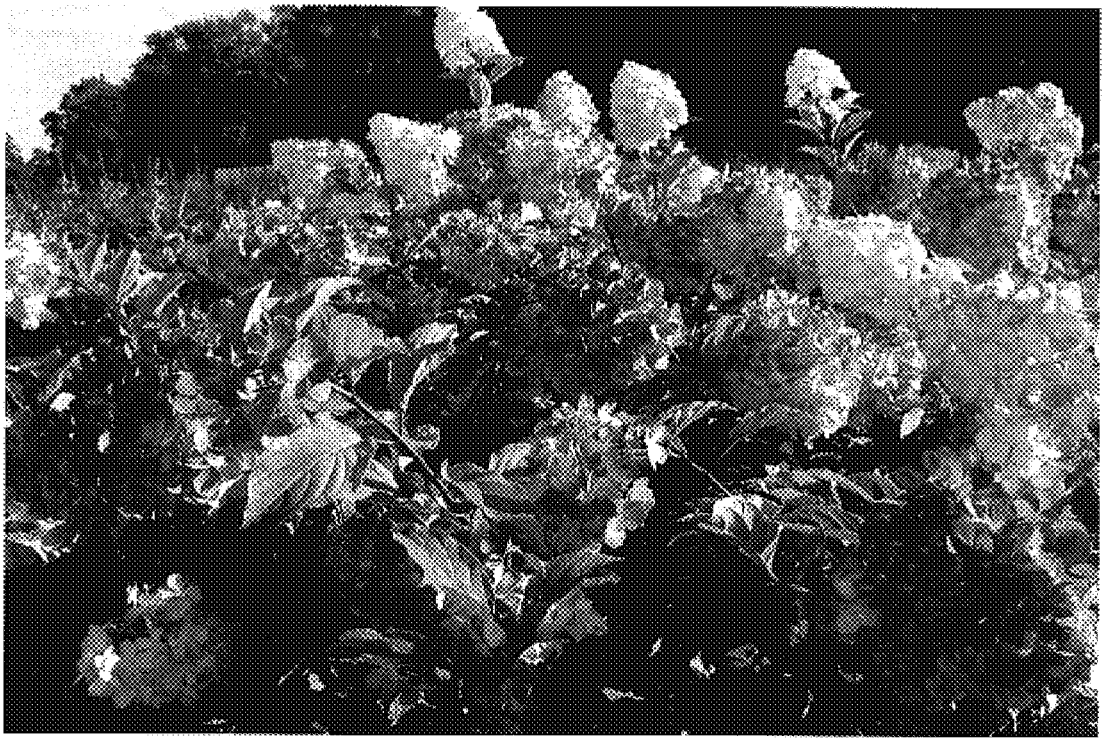
FIG. 1 is a side view of 'RENHY' in early fall and shows the multicolored effect of the inflorescences and the deep red coloration of mature flowers.
Figure 2:
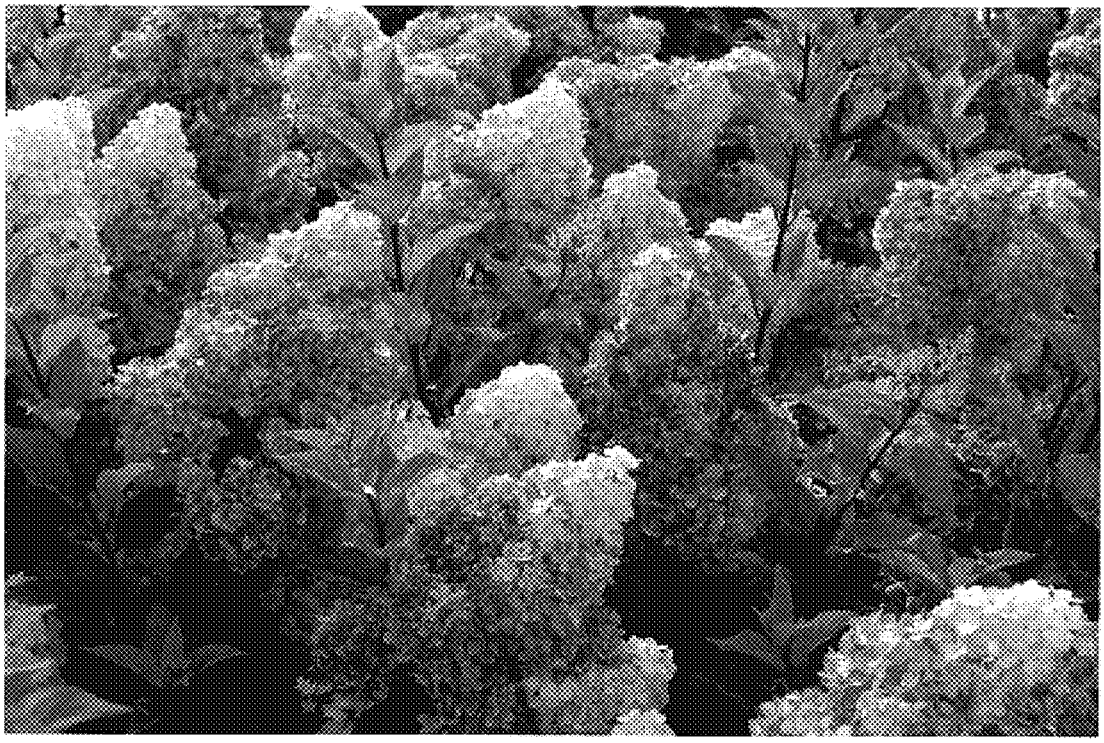
Figure 3:
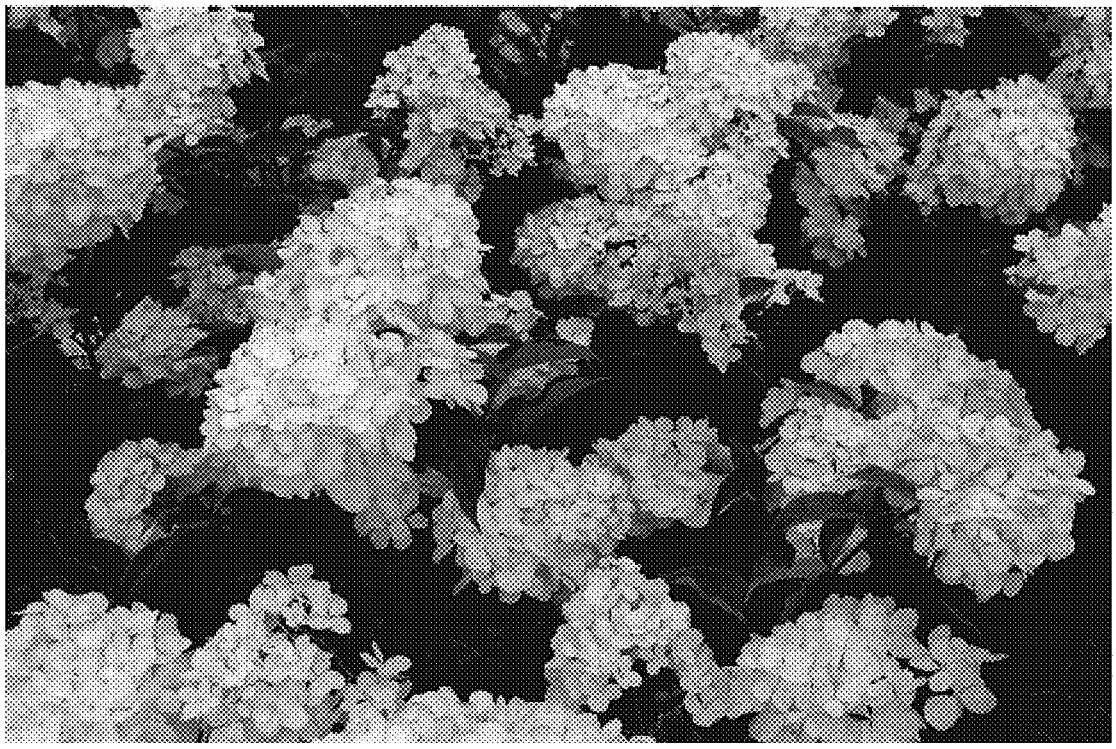
FIG. 3 depicts the color of the inflorescences in mid summer during the first flush of bloom.
Figure 4:
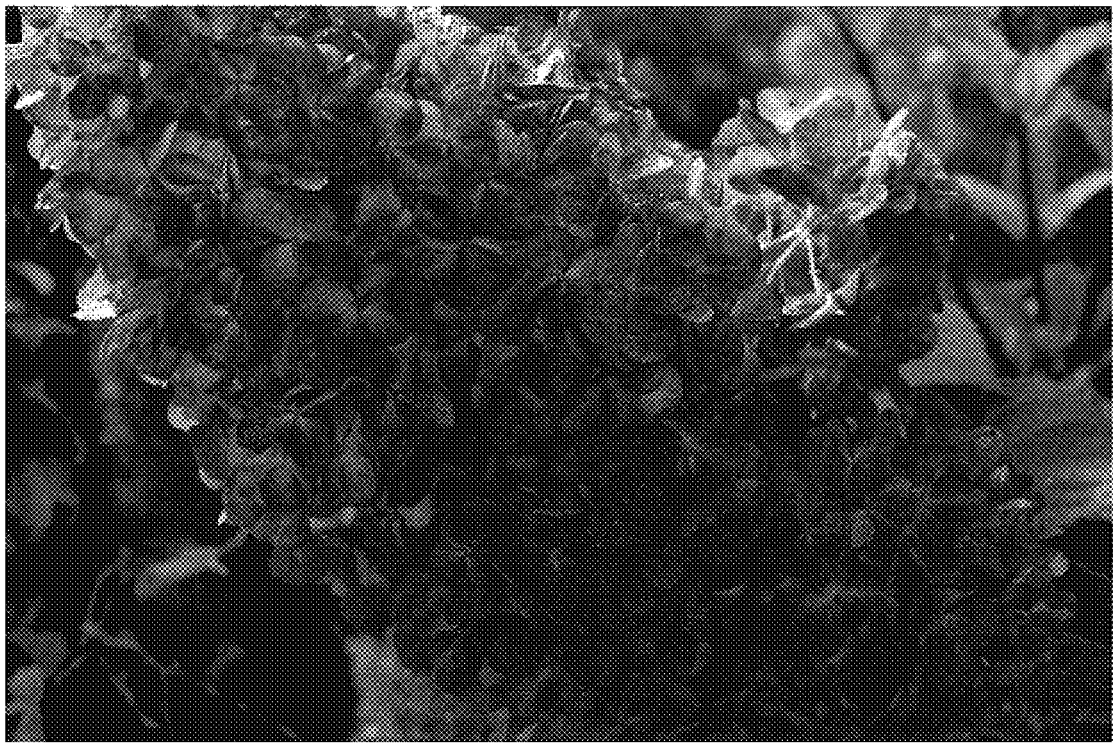

A close-up view of an inflorescence in late summer is depicted in FIG. 4.

The colors in the photographs are as close as possible with the photographic and printing technology utilized. The color values cited in the detailed botanical description accurately describe the colors of the new *Hydrangea*.

BOTANICAL DESCRIPTION OF THE PLANT

The following is a detailed description of the new cultivar as observed on plants grown outdoors in a trial garden for 5 years in Gorron, France and of plants two years in age as grown under greenhouse conditions in St. Paul, Minn. Phenotypic differences may be observed with variations in environmental, climatic, and cultural conditions. The color determination is in accordance with the 2001 R.H.S. Colour Chart of The Royal Horticultural Society, London, England, except where general color terms of ordinary dictionary significance are used.

Botanical classification: 'RENHY' is a cultivar of *Hydrangea paniculata*.

General Description:

*Blooming period.*—From mid July to mid October in France.

*Plant habit.*—Erect through mid summer, becoming supple and cascading in late summer through fall.

*Height and spread.*—Reaches about 2.5 m in height and 1.5 m width.

*Cold hardiness.*—U.S.D.A. Zone 4.

*Culture.*—Grows best in moist but well-drained, humus-rich soil in full sun to partial shade.

*Diseases and pests.*—No susceptibility or resistance to diseases or pests has been observed.

*Root description.*—Fibrous.

Growth and Propagation:

*Propagation.*—Softwood stem cuttings.

*Root initiation.*—About 2 weeks in summer under greenhouse conditions without supplemental lighting and about 3 weeks in winter with bottom heat in France.

*Time required to produce a salable crop.*—A plug of a rooted cutting finishes in a P9 container grown outdoors in about 5 to 6 months.

Stem Description:

*Shape shape.*—Round, solid.

*Stem color.*—New wood 178A, mature wood 166A, old wood (dormant); 199B.

*Stem diameter.*—Average of 5 mm on average.

*Stem surface.*—Pubescent when young becoming glabrous.

*Internode length.*—Average of 5 cm.

*Branching.*—A single dormant stem will produce an average of 5 primary branches. Subsequent branching is determined by pinching; 2 stems develop per pinched node.

Foliage Description:

*Leaf shape.*—Elliptic.

*Leaf division.*—Simple.

*Leaf base.*—Cuneate.

*Leaf apex.*—Primarily acuminate.

*Leaf venation.*—Pinnate, recessed, color 149C on upper surface and 144D on lower surface.

*Leaf margin.*—Serrated.

*Leaf attachment.*—Petiolate.

*Leaf arrangement.*—Opposite.

*Leaf surface.*—Glabrous on upper and lower surface.

*Leaf color.*—Newly formed leaves upper surface; 137C, newly formed leaves lower surface; 138B, mature leaves upper surface; 137A to 139A, mature leaves lower surface; 138A.

*Petioles.*—Average of 2 cm in length and 4 mm in width, sulcate in shape, stipules absent, 178A in color.

Flower Description:

*Inflorescence type.*—Broadly pyramidal panicles of sterile flowers.

*Lastingness of inflorescence.*—Persistent but color is retained for 4 to 6 weeks before browning.

*Inflorescence size.*—Average of 12 cm in diameter and 17 cm in length.

*Inflorescence number.*—One per stem, new shoots develop throughout the summer.

*Flower number.*—Numerous, approximately 200 per inflorescence.

*Fragrance.*—None.

*Flower buds.*—Up to 6 mm in length and 4 mm in width prior to opening, color is 145B changing to 145C prior to opening.

*Peduncles.*—Average of 4 cm in length and 4.5 mm in width, 178A in color, surface is glabrous.

*Bracts.*—Not observed.

*Pedicels.*—8 to 12 mm in length and 1 mm in width, color is 145D flushed with 62C at peak bloom, surface is glabrous.

*Flower size.*—Average of 2.2 cm in diameter and 1 cm in depth.

*Sepals.*—4, orbicular, aposepalous, partially overlapping, rounded apex, cuneate base, entire margin, average of 1 cm in length and 1 cm in width, glabrous on both surfaces, color upper and lower surface; 155A when opening with some flushed with 62C to 62D, changes to 62A to 62B mottled with 155A, becoming mottled as they further mature with 64A to 64B, and at final maturity become mottled with 53A, all of the above colors can exist in a mottled or blended pattern at maturity, dry and fade to about 161B.

*Center (eye) size.*—2 mm in diameter, color is 155A when flowers first open changing 160A at maturity.

*Reproductive organs.*—None, only sterile flowers observed.

We claim:

1. A new and distinct cultivar of *Hydrangea* plant named 'RENHY' as herein illustrated and described.

* * * * *